(12) United States Patent
Rodefeld

(10) Patent No.: US 11,920,597 B2
(45) Date of Patent: Mar. 5, 2024

(54) BOUNDARY LAYER POWERED CIRCULATORY ASSIST DEVICE

(71) Applicant: Indiana University Research and Technology Corporation, Bloomington, IN (US)

(72) Inventor: Mark D. Rodefeld, Carmel, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 0 days.

(21) Appl. No.: 17/654,321

(22) Filed: Mar. 10, 2022

(65) Prior Publication Data

US 2022/0290696 A1 Sep. 15, 2022

Related U.S. Application Data

(60) Provisional application No. 63/159,235, filed on Mar. 10, 2021.

(51) Int. Cl.

| F04D 13/04 | (2006.01) |
|---|---|
| A61M 60/122 | (2021.01) |
| A61M 60/232 | (2021.01) |
| A61M 60/35 | (2021.01) |
| A61M 60/405 | (2021.01) |
| A61M 60/416 | (2021.01) |

(Continued)

(52) U.S. Cl.
CPC ........... *F04D 13/04* (2013.01); *A61M 60/122* (2021.01); *A61M 60/232* (2021.01); *A61M 60/35* (2021.01); *A61M 60/405* (2021.01); *A61M 60/416* (2021.01); *F04D 1/00* (2013.01); *F04D 7/04* (2013.01)

(58) Field of Classification Search
CPC .............. A61M 60/122; A61M 60/232; A61M 60/178; A61M 60/416; A61M 60/35; A61M 60/216; A61M 60/405; F04D 13/04
USPC ................................ 417/375, 391, 405–407
See application file for complete search history.

(56) References Cited

U.S. PATENT DOCUMENTS

| 3,487,784 | A | * | 1/1970 | Rafferty .............. A61M 60/827 |
|---|---|---|---|---|
| | | | | 415/80 |
| 5,145,333 | A | | 9/1992 | Smith |
| 6,152,704 | A | | 11/2000 | Aboul Hosn et al. |

(Continued)

FOREIGN PATENT DOCUMENTS

| CN | 110575577 | 12/2019 |
|---|---|---|
| DE | 102010011998 | 9/2010 |

(Continued)

OTHER PUBLICATIONS

Cysyk, Joshua et al., "Chronic In Vivo Test of a Right Heart Replacement Blood Pump for Failed Fontan Circulation," ASAIO Journal, 8 pgs. 2019.

(Continued)

*Primary Examiner* — Kenneth J Hansen
(74) *Attorney, Agent, or Firm* — John V. Daniluck; Dentons Bingham Greenebaum LLP

(57) ABSTRACT

Apparatus and methods for driving a circulatory assist device with motive power from a fluid motor. In one example a parallel plate Tesla-type of motor extracts power from the circulatory system of a biological unit to drive a non-positive displacement pump and increase blood pressure in the biological unit.

18 Claims, 9 Drawing Sheets

(51) Int. Cl.
*F04D 1/00* (2006.01)
*F04D 7/04* (2006.01)

(56) References Cited

U.S. PATENT DOCUMENTS

| | | | |
|---|---|---|---|
| 8,777,832 | B1 | 7/2014 | Wang et al. |
| 9,585,746 | B2 | 3/2017 | Yoshida et al. |
| 9,662,432 | B2 | 5/2017 | Gopalakrishna et al. |
| 10,639,103 | B2 | 5/2020 | Piskin et al. |
| 10,729,529 | B2 | 8/2020 | Pekkan et al. |
| 11,311,713 | B2 | 4/2022 | Pekkan |
| 2008/0021368 | A1 | 1/2008 | Dasi et al. |
| 2020/0306432 | A1 * | 10/2020 | Pekkan ............... A61M 60/857 |

FOREIGN PATENT DOCUMENTS

| | | | |
|---|---|---|---|
| EP | 3366332 | 8/2018 | |
| KR | 100971262 | 7/2010 | |
| WO | 2018200782 | 11/2018 | |
| WO | WO-2019173495 A1 * | 9/2019 | .......... A61M 60/148 |
| WO | 2019238677 | 12/2019 | |

OTHER PUBLICATIONS

Ali, Shujan et al., Interim Report for CFD Analysis of Self-Powered VAD Device, 48 pgs. Jul. 22, 2020.
Izraelev, Valentin, et al., "A Passively Suspended Tesla Pump Left Ventricular Assist Device," ASAIO Journal , pp. 556-561 2009.
Mock Circulatory System Tests for the Self-Powered Fontan Pump, Figliola Lab, Clemson University, 21 pgs. Jul. 3, 2020.
Weinstein et al., "The use of the Berlin Heart EXCOR in patients with functional single ventricle," J. Thorac. Cardiovasc. Surg., vol. 147, No. 2, pp. 697-705 Feb. 2014.
Khambadkone et al., Basal Pulmonary Vascular Resistance and Nitric Oxide Responsiveness Late After Fontan-Type Operation, Circulation, pp. 3204-3208 Jul. 2003.
Zhu et al., "Cavopulmonary Support with a Microaxial Pump for the Failing Fontan Physiology," ASAIO Journal, vol. 61, pp. 49-54 2015.
Derk et al., "Novel techniques of mechanical circulatory support for the right heart and Fontan circulation," International Journal of Cardiology vol. 176, pp. 828-832 2014.
McRae, "Long-term Issues After the Fontan Procedure," AACN Adv. Crit. Care, vol. 24, pp. 264-282 2013.

* cited by examiner

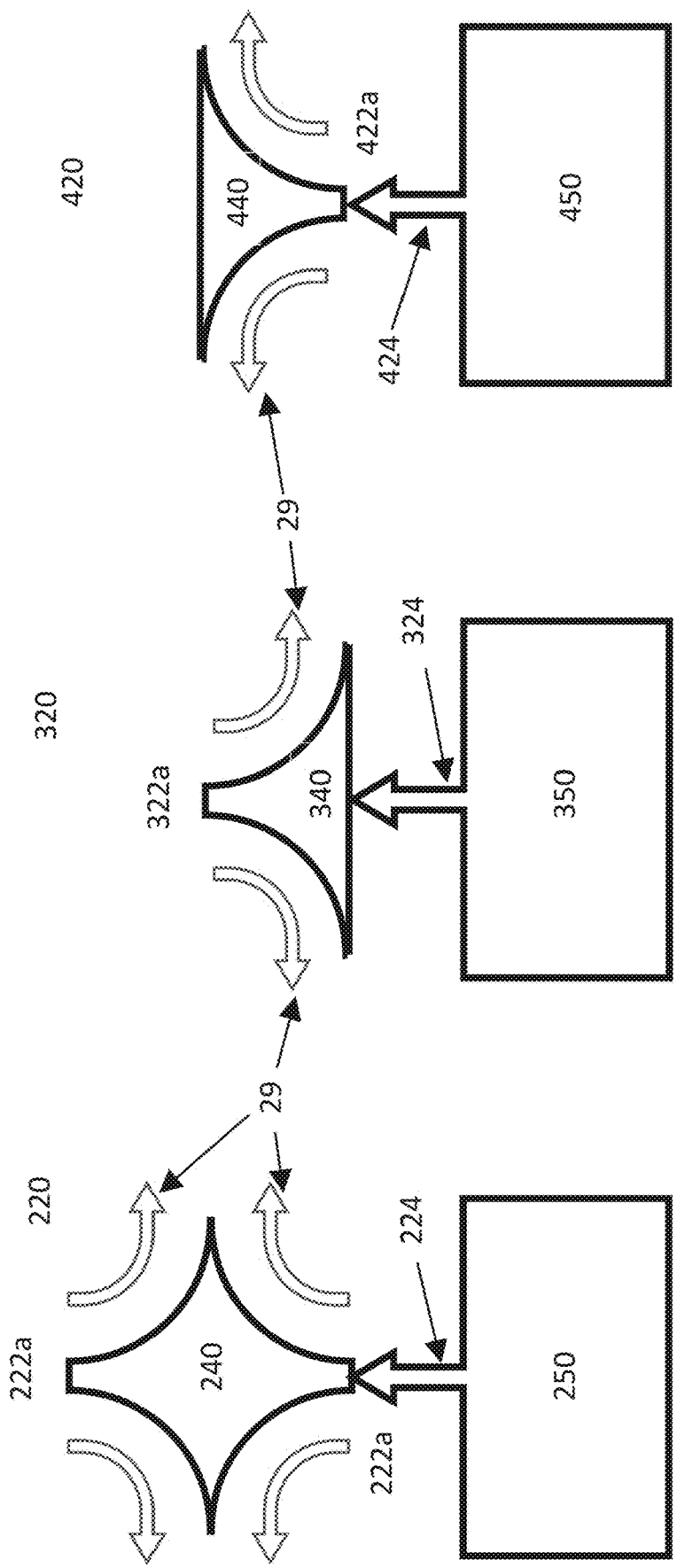

BOUNDARY LAYER POWERED CIRCULATORY ASSIST DEVICE

CROSS REFERENCE TO RELATED APPLICATION

This application claims the benefit of priority to U.S. Provisional Patent Application Ser. No. 63/159,235, filed Mar. 10, 2021, BOUNDARY LAYER POWERED CIRCULATORY ASSIST DEVICE, incorporated herein by reference.

FIELD OF THE INVENTION

Various embodiments of the invention relate generally to the field of pumping assemblies including a motor driving a blood pump, including motors driven hydraulically, including non-positive displacement pumps of rotary design, and including those assemblies suitable for permanent implantation in animals for use in circulatory support as well as those suitable for industrial and laboratory use.

BACKGROUND OF THE INVENTION

Some children are born missing half their heart. Known as single ventricle heart disease, it is the leading cause of death in children less than one year of age from any structural birth defect. One common anatomic variant is Hypoplastic Left Heart Syndrome. Until recently this condition was not compatible with survival. Beginning in the 1970's, developments in the surgical treatment of single ventricle heart disease have resulted in a means of not only survival, but also reasonable quality of life for survivors at least into early adulthood. Current therapy includes a series of 3 staged open heart procedures. While these procedures offer hope for survival, they remain problematic and notorious for instability and mortality. The staged surgical reconstruction of the circulatory system culminates in a univentricular Fontan circulation, eponymous with Dr. Francis Fontan who first described the repair in 1971.

In a univentricular Fontan circulation, the single ventricle (pumping chamber) is committed to provide blood flow to the body. Opposed to a normal 2-ventricle circulation, however, blood flow through the lungs is not supported by a ventricular power source; it should rather flow through the lungs passively. Therefore, the motive force for blood flow through the lungs rests upon systemic venous pressure alone. As a consequence, systemic venous pressure is markedly elevated and systemic venous return is significantly altered. This sets up a new set of hemodynamic problems, described by de Leval as the Fontan paradox, in which elevated systemic venous pressure coexists with relative pulmonary arterial hypotension. Preload to the single ventricle is reduced, as well as cardiac output. Patients with a univentricular Fontan circulation are therefore at high risk for late Fontan failure and attrition.

The late consequences of this circulatory arrangement are now an emerging public health concern. Thousands of patients who survive Fontan palliation are expected to present with Fontan failure. The insidious complications of chronically elevated systemic venous pressure include hepatic and gut dysfunction, protein losing enteropathy, leg swelling, and collection of fluid in the abdominal and chest cavities. The insidious complications of chronically reduced preload include late ventricular diastolic dysfunction, and poor systemic tissue perfusion. Targeted medical therapeutic options for Fontan failure do not exist. For example, while diuretic therapy may improve symptoms of increased tissue/organ edema, it does so at the expense of circulating blood volume which is helpful to Fontan circulatory homeostasis. Similarly, although the use of inotropic support may improve myocardial contractility, this is of marginal impact in an insufficiently filled ventricle. Heart transplantation is a poor end-stage option: Transplantation carries morbidity of its own, and the donor pool is limited. Few patients will ultimately be candidates or receive a donor organ for transplantation.

The development of a permanent right-sided circulatory support device directly addresses the Fontan paradox and will improve late quality of life and outcomes for those born with single functional ventricle. One aspect of some embodiments has been to include power sources to support the univentricular Fontan circulation. The placement of a power source at the level of the total cavopulmonary connection effectively empowers the univentricular Fontan circulation by placing a right ventricle equivalent back into a circulation that lacks one. By simultaneously reducing systemic venous pressure and improving ventricular preload, normal 2-ventricle physiology can be effectively restored.

Prior applications of existing blood pump technology have been contemplated to address the problem of powering the Fontan circulation. These have consisted primarily of applying intravascular unidirectional axial flow pumps to augment Fontan flow. The concept of cavopulmonary assist was introduced in 2003 with the simultaneous use of 2 unidirectional axial flow pumps (Rodefeld et al, Ann Thoracic Surg). This has limitations, however, as one-way flow devices will cause undesirable back-pressure elevation in the opposing vena caval territory. Other groups have followed with modifications of axial flow pump designs intended to operate in the low-pressure systemic venous circulation. This has also included a modification of the preferred TCPC Fontan venous pathway to a 3-way pathway so that the pathway better accommodates a unidirectional pump in a common unidirectional outflow limb. Although in theory this is possible, the 3-way vascular configuration is not the preferred hemodynamic pathway in an unsupported Fontan circulation.

What follows are various improvements in the field of non-positive displacement, motor-driven circulatory pumps that overcome some of the disadvantages of existing systems.

SUMMARY OF THE INVENTION

It is a further aspect of some embodiments to provide a means for pumping blood or other liquids using a motor that produces power from a pressurized flowing fluid.

Yet another aspect of some embodiments includes the use of a motor that uses a boundary layer effect to provide motive power to a pump.

Yet another aspect of some embodiments pertains to providing motive power by the flow of blood to a Tesla-type of motor.

It is a further aspect of some embodiments to provide a permanent Fontan pump which will afford the opportunity to address right/left lung blood flow disparity.

It is a further aspect of some embodiments to provide a permanent Fontan blood pump which will afford the opportunity to address vessel stenoses at the time of device implantation.

It will be appreciated that the various apparatus and methods described in this summary section, as well as elsewhere in this application, can be expressed as a large number of different combinations and subcombinations. All such useful, novel, and inventive combinations and subcombinations are contemplated herein, it being recognized that the explicit expression of each of these combinations is unnecessary.

BRIEF DESCRIPTION OF THE DRAWINGS

FIG. 10A is a schematic representation of a motor driving an impeller according to another embodiment of the present invention.

FIG. 10B is a schematic representation of a motor driving an impeller according to another embodiment of the present invention.

FIG. 10C is a schematic representation of a motor driving an impeller according to another embodiment of the present invention.

ELEMENT NOMENCLATURE

Figure 1:
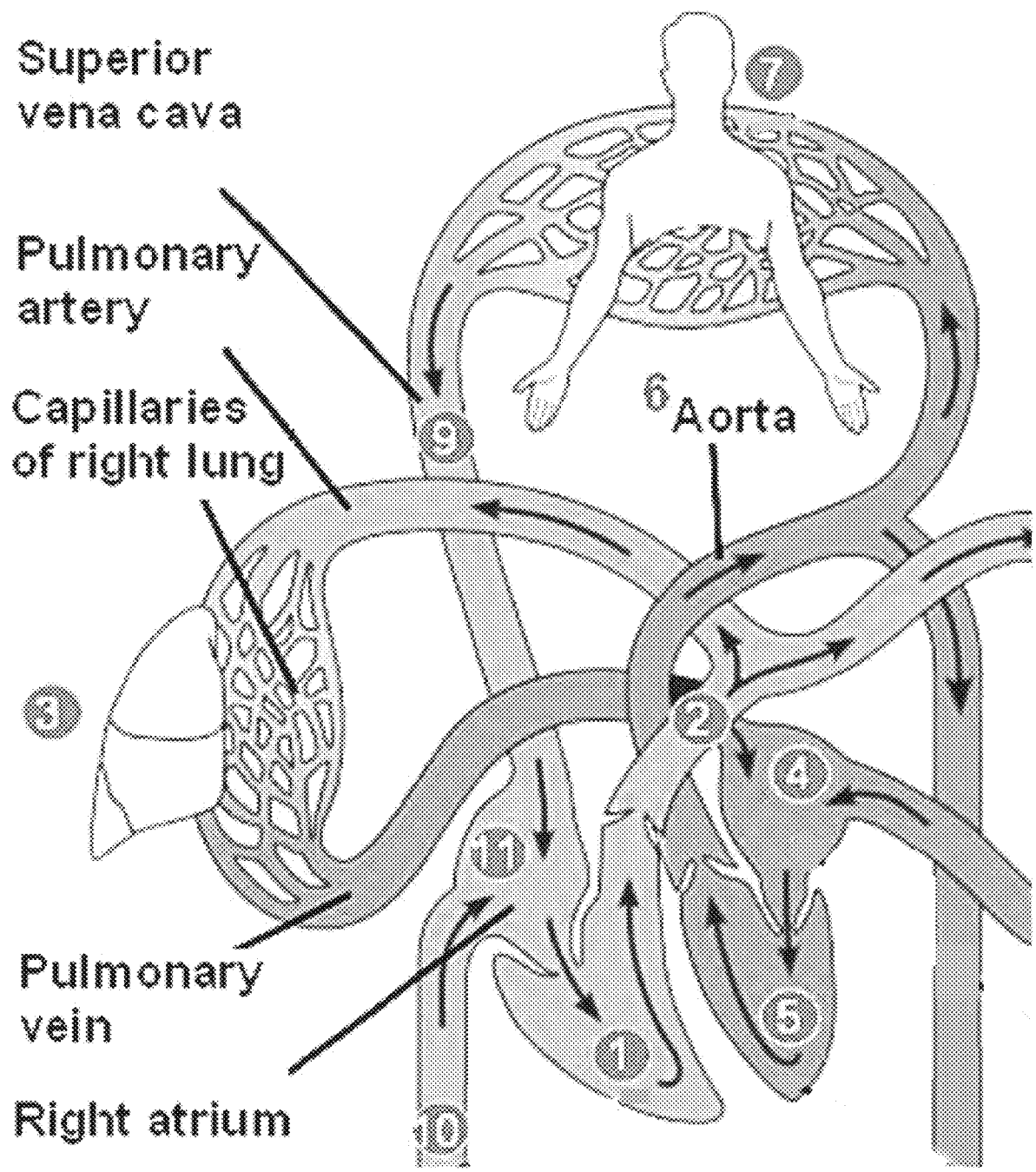
FIG. 1 is a schematic representation of a portion of the circulatory system of a human.

The following is a list of element numbers and at least one noun used to describe that element. It is understood that none of the embodiments disclosed herein are limited to these nouns, and these element numbers can further include other words that would be understood by a person of ordinary skill reading and reviewing this disclosure in its entirety.

| | |
|---|---|
| 10 | Circulatory system |
| 12 | Fontan junction |
| 14 | source of higher pressure |
| 16 | source of lower pressure |
| 20 | Implantable pumping assembly |
| 22 | Housing |
| a | inlet |
| b | outlet |
| 24 | Shaft |
| a | solid portion |
| b | hollow portion; return flow path |
| c | drain |
| 25 | fluid conduit; shunt |
| a | inlet |
| b | outlet |
| c | nozzle |
| d | manifold |
| 26 | bearings |
| 28 | bearing supports, strut |
| 29 | direction of flow |
| 40 | pump; impeller |
| 42 | viscous impelling surface |
| 44 | blade |
| a | surface |
| 46 | flow passage |
| a | outlet |
| 50 | Motor; means for providing power by action of a fluid boundary layer; boundary-layer turbine, cohesion-type turbine, or Prandtl-layer turbine |
| 52 | peripheral inlet |
| 54 | stack |
| a | periphery |
| b | center; central region |
| c | stack drain flow path |
| 56 | plates; disk |
| a | periphery |
| b | center |
| c | flow exit |

DESCRIPTION OF THE PREFERRED EMBODIMENT

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates. At least one embodiment of the present invention will be described and shown, and this application may show and/or describe other embodiments of the present invention, and further permits the reasonable and logical inference of still other embodiments as would be understood by persons of ordinary skill in the art.

It is understood that any reference to "the invention" is a reference to an embodiment of a family of inventions, with no single embodiment including an apparatus, process, or composition that should be included in all embodiments, unless otherwise stated. Further, although there may be discussion with regards to "advantages" provided by some embodiments of the present invention, it is understood that yet other embodiments may not include those same advantages, or may include yet different advantages. Any advantages described herein are not to be construed as limiting to any of the claims. The usage of words indicating preference, such as "various embodiments" or "preferably," refers to features and aspects that are present in at least one embodiment, but which are optional for some embodiments, it therefore being understood that use of the word "preferably" implies the term "optional."

The use of an N-series prefix for an element number (NXX.XX) refers to an element that is the same as the non-prefixed element (XX.XX), except as shown and described. As an example, an element 1020.1 would be the same as element 20.1, except for those different features of element 1020.1 shown and described. Further, common elements and common features of related elements may be drawn in the same manner in different figures, and/or use the same symbology in different figures. As such, it is not necessary to describe the features of 1020.1 and 20.1 that are the same, since these common features are apparent to a person of ordinary skill in the related field of technology. Further, it is understood that some features 1020.1 and 20.1 may be backward compatible, such that a feature of a later discussed embodiment (NXX.XX) may include features compatible with other various embodiments that were discussed earlier (MXX.XX), as would be understood by those of ordinary skill in the art. This description convention also applies to the use of prime ('), double prime ("), and triple prime ("') suffixed element numbers. Therefore, it is not necessary to describe the features of 20.1, 20.1', 20.1", and 20.1''' that are the same since these common features are apparent to persons of ordinary skill in the related field of technology.

Although various specific quantities (spatial dimensions, temperatures, pressures, times, force, resistance, current, voltage, concentrations, wavelengths, frequencies, heat transfer coefficients, dimensionless parameters, etc.) may be stated herein, such specific quantities are presented as examples only, and further, unless otherwise explicitly noted, are approximate values, and should be considered as if the word "about" prefaced each quantity. Further, with discussion pertaining to a specific composition of matter, that description is by example only, and does not limit the applicability of other species of that composition, nor does it limit the applicability of other compositions unrelated to the cited composition.

This document may use different words to describe the same element number, or to refer to an element number in a specific family of features (NXX.XX). It is understood that such multiple, different words are not intended to provide a redefinition of any language herein. It is understood that such words demonstrate that the particular feature can be considered in various linguistical ways, such ways not necessarily being additive or exclusive.

Various embodiments of the present invention pertain to apparatus and methods for providing an energy increase in a flow system. Although various embodiments will be described with regards to circulatory systems of biological units, it is understood that the various designs herein are applicable not only as implanted devices in a living organism, but further as pumping devices in industrial and laboratory settings.

Various embodiments include a centrifugal pump or impeller X40 that is powered by a hydraulic motor X50. In some applications, the impeller imparts an increase in the energy of the fluid by centrifugal action of the impeller, such as by rotating blades, a rotating smooth surface, or combinations of both.

The impeller is preferably incorporated onto a portion of a rotating body driven by a hydraulic motor. The hydraulic motor is preferably but not necessarily provided with fluid from a pressure that is higher than the pressure received at the inlet of the impeller or provided at the outlet of the impeller, and is further of the same type of fluid to which the impeller is imparting work. By powering the hydraulic motor with a higher pressure source of the same fluid, it is not necessary to isolate the fluid providing motive power from the fluid whose energy is being increased. Although it is desirable in some embodiments to keep the motive fluid separate from the impelled fluid, in some embodiments the two fluids are of the same chemistry and the same flow system, the mixing of the two fluids does not present a problem to the biological unit or the industrial/laboratory flow system. However, yet other embodiments of the present invention contemplate the motive flow fluid being different than the impelled fluid, provided that the introduction of the motive fluid into the impelled fluid does not present a problem to the biological unit or to the flow system.

In a preferred embodiment, the motive power for the fluid is provided from a relatively high pressure source in the circulatory system, such as the output of the left ventricle. Blood at about the same pressure as blood at the output of the left ventricle is provided by way of an implanted shunt to the inlet of the hydraulic motor. This highest pressure blood provides motive power to the impeller. As this supply of blood exits the hydraulic motor, it is then provided back to the circulatory system in either a "closed" system (in which the motive flow blood flows through a second implanted shunt to a source of lower pressure, such as the inlet of the left atrium) or by way of an "opened" system in which the higher pressure blood providing the mode of power then mixes in any of a variety of ways with the blood flowing over the impeller.

After performing work by the hydraulic motor, the lowered pressure blood can then either: (1) exit through an outlet support and a corresponding static outlet, and into the implanted shunt and back to a lower source (such as to the left atrium in some closed loop embodiments; or (2) exist through a surface of the pump X40 having a surface with appropriately low static pressure at the surface. Preferably, the motor and pump (i.e., the rotor) are placed within an internal passageway of a support housing X22 that has a central portion that is free and clear around the rotor, so as to provide relatively low pressure losses in the event that the rotor stops turning.

In various embodiments shown herein, the impellers can be of any type, and examples are shown and described herein, and further in either of two PCT applications referenced herein. It is understood that any of these impellers, or others, can be integrated with the hydraulic motors described herein.

A motor X50 in some embodiments may be a Tesla-type turbine that is preferably a bladeless turbine. The Tesla turbine may also be known as a boundary-layer turbine, cohesion-type turbine, or Prandtl-layer turbine (after Ludwig Prandtl), because it uses the boundary-layer effect and in some embodiments does not use a fluid impinging upon the blades as in a conventional turbine.

One aspect of a boundary-layer motor turbine is that in order to attain higher efficiency, the changes in the velocity and direction of movement of fluid should be as gradual as possible. Therefore, the propelling fluid of Tesla turbine moves in natural paths or stream lines of least resistance.

A Tesla-type turbine in one embodiment includes a set of smooth disks or plate X56, preferably with one or more nozzles X25c applying a moving fluid to the edge of the disk. The fluid drags on the disk by means of viscosity and the adhesion of the surface layer of the fluid. As the fluid slows and adds energy to the disks, it spirals into the center exhaust.

Preferably, the disks X56 should be relatively thin, especially at the edges or periphery, in order to minimize turbulence as the fluid leaves the disks. In some embodiments it is helpful to increase the number of disks as the flow rate increases. Maximum efficiency sometimes comes in this system when the inter-disk spacing approximates the thickness of the boundary layer. Since boundary layer thickness is dependent on viscosity and pressure, some of the embodiments discussed herein include a boundary-layer driven motor X50 that is adapted and configured to use blood flowing from a higher pressure source to a lower pressure source as a source of power.

In some embodiments the efficiency of a motor X50 is a function of power output. A moderate load makes for high efficiency. Too heavy a load may increases the slip in the turbine and lowers the efficiency; with too light a load, little power is delivered to the output, which also decreases efficiency (to zero at idle). In some embodiments the efficiency is increased by matching the internal impedance of the motor X50 to the impedance of the pump X40.

Although the various embodiments of the present invention contemplate application to any fluid and any environment, some embodiments are adapted and configured to be used in a Fontan junction. The bioengineering considerations to accomplish cavopulmonary assist are unique in a univentricular Fontan circulation. A chronic Fontan pump should: 1) deliver low pressure, high volume flow similar to normal right ventricular hemodynamics; 2) augment flow in 4 directions with axially opposed inflow and orthogonally related bidirectional outflow; 3) avoid thrombogenicity, preferably with a bearingless and seal-less design; 4) have an expected durability of decades; 5) utilize a power source that is realistic for such long-term use; 6) should not obstruct flow in the Fontan venous pathway—whether the pump is functional or not.

A chronic rotary blood pump according to one embodiment of the present invention designed to support the Fontan circulation is surgically implanted into the total cavopulmonary connection (TCPC). This is the anatomic junction created between the superior and inferior vena cavae and the right and left pulmonary arteries during Fontan surgery. This anatomic configuration is in the shape of a '+' and is the preferred construction for passive venopulmonary blood flow in Fontan patients. The surgical implantation of a permanent cavopulmonary assist device in this location is technically similar to a Fontan conversion operation, and therefore reasonable to perform. It includes cardiopulmonary bypass, but not cardioplegic arrest.

Once implanted, the pump preferably provides at least about one to fifteen mm Hg pressure augmentation, and more preferably about two to ten mm Hg pressure augmentation to Fontan venous flow. Accordingly, this decreases upstream systemic venous pressure, and increases pulmonary arterial pressure, translating to increased transpulmonary blood flow, increased preload, and ultimately increased cardiac output. This low pressure pumping action provides a transformative improvement in circulatory status by restoring more stable 2-ventricle physiology.

Some embodiments of the present invention pertain to a means to self-power the pump, rather than use an external or internal power source. The viscous pump can be powered by a turbine or other hydraulic motor using systemic arterial pressure which is a higher pressure source than exists in the right-sided circulation. Using the pressure energy reserve in the systemic arterial circulation, the pressure differential can be used to hydraulically power a pump to augment flow in the low-pressure right-sided circulation. This would be of significant value because it could simplify the device, make it more user-friendly, and preferably eliminate the need for continuous external power input.

Various embodiments preferably include one or more of the following aspects: 1) simplified device; 2) reduced failure risk and improved long-term durability; 3) reduced/minimal/no maintenance (place it and forget it), 4) activity responsiveness (exercise will increase systemic blood pressure, which will in turn increase right-sided circulatory support); 5) pumping can be phasic (pulsatile) and therefore more physiologic because drive will come from a pulsatile source; 6) eliminates the need for transcutaneous drivelines or complex wireless charging, Existing blood pumps are sometimes limited by the need for a continuous, external power source to ensure continuous operation of the device. This includes percutaneous drivelines which penetrate the skin and are a source for infection and driveline failure. This also imposes a heavy societal burden on the patient (unable to shower, swim, etc).

A self-powered viscous pump can theoretically be placed and "forgotten". It will self-sustain, and no maintenance is required (other than oral anticoagulation). It would eliminate drivelines and infection risk. It would enhance lifestyle for patients allowing them untethered benefit of the device, with no restriction whatsoever.

Some embodiments of the invention propose the use of systemic blood pressure and a "shunt" to provide a high-pressure source of blood flow to energize the viscous pump. The high-pressure inflow would actuate a motor, which would in turn actuate a compressor (i.e. such as a viscous pump or bladed pump) to augment the lower pressure right-sided circulation. In some embodiments, a second shunt is used to provide flow from the hydraulic motor to a low-pressure source of blood flow.

In the text and drawings of this document reference will be made to the use of a pump in the circulatory system of an animal. It is recognized still further that the apparatus and methods described herein further pertain to the pumping of a fluid in any similar arrangement of fluid passageways.

Various embodiments of the present invention pertain to a pump adapted and configured to provide a pressure assist to the cavopulmonary system of an animal. In some embodiments, the pump is packaged within a housing that is adapted and configured to be placed within the circulatory system of the animal on a permanent basis.

In some embodiments, the pump is of the non-positive displacement variety, and provides an increase in energy to the pump fluid by centrifugal action. Preferably, the centrifugal assist is applied to the working fluid by a viscous operation on the surface of a rotating element, although other embodiments contemplate that the centrifugal assist is provided by any of a variety of surface motive flow features that extend outwardly from the surface. In some embodiments, the rotating element is axisymmetric, whereas in other embodiments the rotor is both axisymmetric and further symmetrical about a plane. Various embodiments of the present invention also pertain to devices and methods for centrifugal blood pumps 40, such as those described in the international PCT applications noted herein.

Some embodiments include a rotor that is suspended about an internal stator by magnetic bearings, rolling bearings, or hydrodynamic bearings, or a combination thereof. Some embodiments include a motor that is centrally located between a pair of pumping surface. In those embodiments having sufficient symmetry (such as axial, planar, or both), there is little or no net thrust of the rotor relative to the stator, and the negligible net thrust can be accommodated by the hydrodynamic bearings. In some other embodiments, the magnetic bearings are adapted and configured to provide both radial support and further a magnetic force that is resistive to any net thrust. These magnetic thrust bearings can include a second pair of magnetic bearings, in additional to a first pair of magnetic bearings that provide radial support of the rotor.

In those embodiments in which the stator has a shape for viscously and centrifugally imparting energy to the fluid (such as a VIP pump), the first pair of magnetic bearings providing radial support may be located proximate to the opposing ends of the rotor, where the outer shape of the rotor is a relatively more parallel to the rotational axis. The second paramagnetic bearings providing thrust support may be located proximate to the center of such a rotor, where the outer shape of the rotor is relatively more parallel to a central plane of symmetry. Still further embodiments include rolling bearings, including pairs of ball, roller, needle, or tapered roller bearings as examples, with each bearing supported one end of the rotor.

One embodiment of the invention disclosed herein solves various problems. The pump (40) disclosed is designed to permanently augment Fontan venous flow. It is modeled morphologically after the temporary percutaneous expandable von Karman viscous impeller pumps which are further described in International patent application Serial No. PCT/US09/59733, filed Oct. 6, 2009, and titled ACTIVE OR PASSIVE ASSISTANCE IN THE CIRCULATORY SYSTEM, and also in International patent application Serial No. PCT/US2012/067648 and titled CAVOPULMONARY VISCOUS IMPELLER ASSIST DEVICE AND METHOD.

This pump in some embodiments is based a spinning disk configuration (viscous impelling pump or VIP) in the shape of a 2-sided centrifugal pump. For some embodiments of the permanent pump disclosed here, however, the impeller can be rigid: It is not required to expand (open) and contract (close). The rotating impeller (X40), suspended in the midst of the housing (X22), draws fluid in from the axial direction by way of inlets X22a (superior and inferior vena cava) and pumps it to the outlets (X23b) which lead to the left and right lungs.

Figure 5:
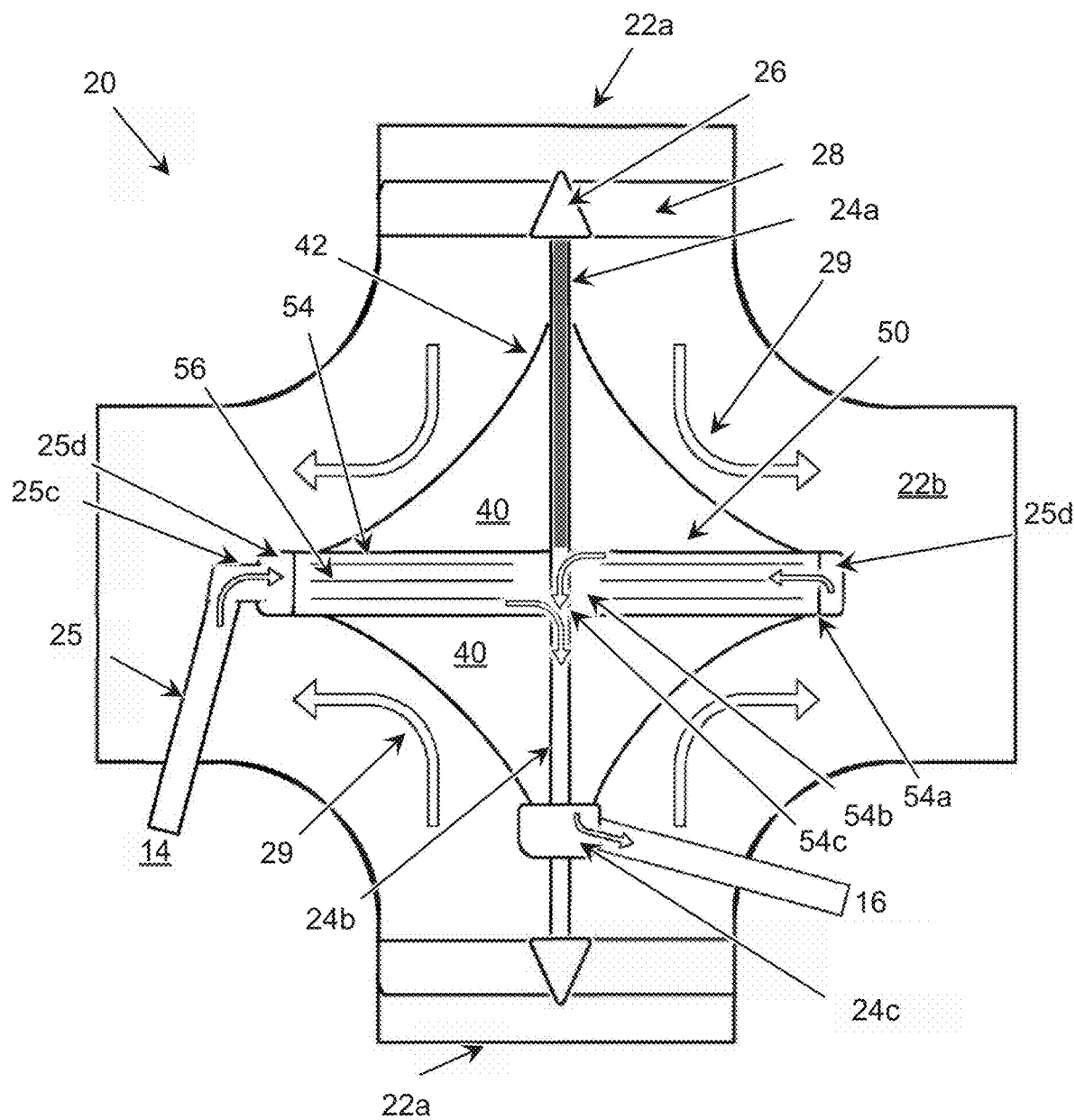
FIG. 5 is a partial cross sectional, schematic representation of the implanted pumping assembly of FIG. 4.

In some embodiments, one half of the VIP pump is placed on one side of the motor, and the other half of the VIP pump is placed on the opposite side of the motor, such that the combined rotor (pump X40 and motor X50) exhibits symmetry about the rotational axis and symmetry about a plane that is perpendicular to the rotational axis. Such a configuration is shown in FIG. 5.

Figure 7:
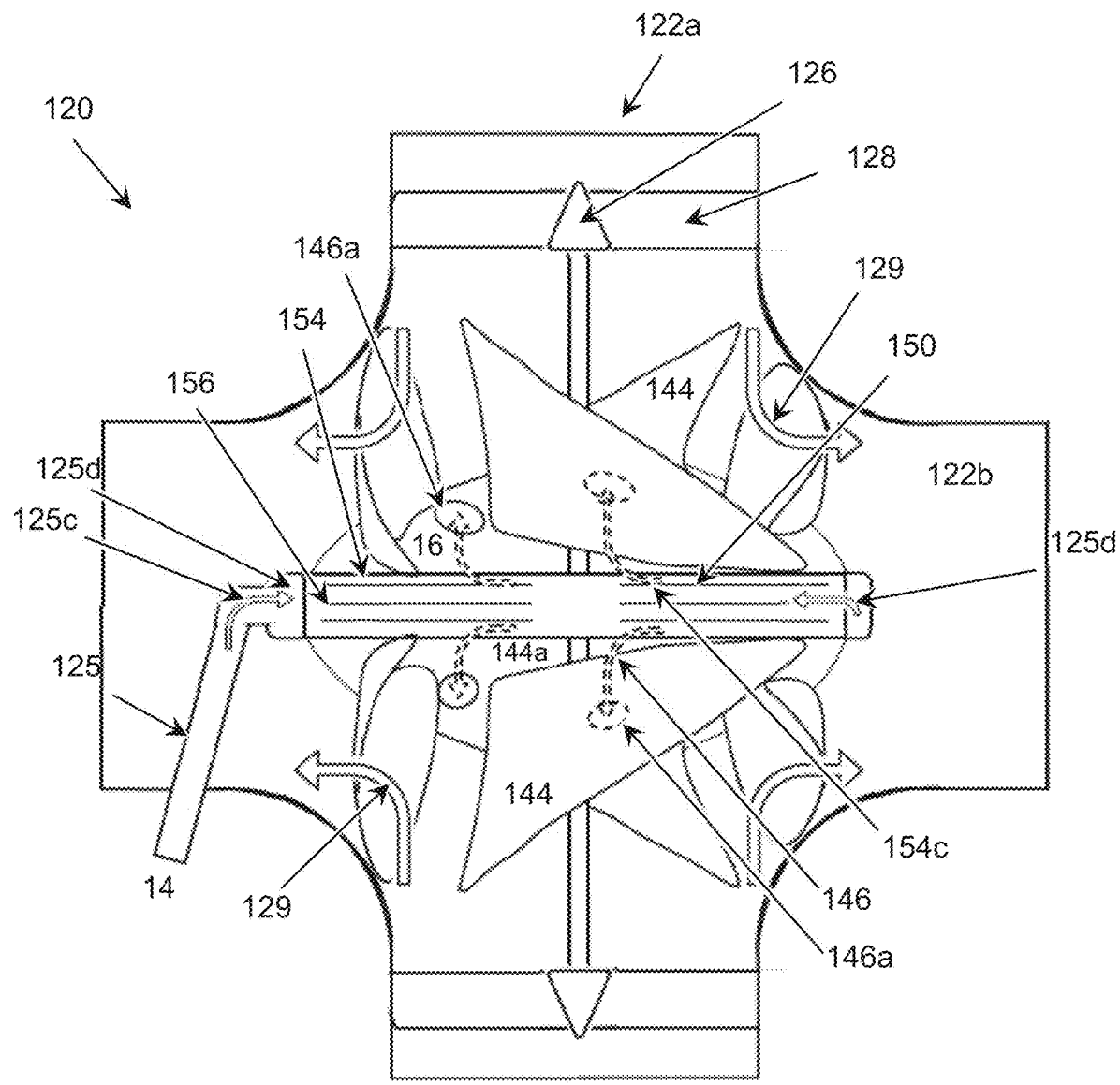
FIG. 7 is a partial cross sectional, schematic representation of the implanted pumping assembly of FIG. 6.

In other embodiments, the pump X40 is of the bladed centrifugal type. One such centrifugal pump is placed on one side of the motor, and another substantially identical centrifugal pump is placed on the opposite side of the motor, such that the combined rotor (pump X40 and motor X50) exhibits symmetry about the rotational axis and symmetry about a plane that is perpendicular to the rotational axis. Such a configuration is shown in FIG. 7.

The various impellers depicted herein can include rotating impeller blades similar to rotating compressor blades, having a curving nature that pushes flow in the direction of rotation of the impeller. Yet others have generally smooth surfaces that impart rotational energy to a flowing fluid by means of viscous drag. Still further impellers contemplated for the invention described herein contemplate combinations of smooth, viscous impelling surfaces and impelling blades. Further description of these devices can be found in the PCT applications referenced herein, with applicability as persons of ordinary skill in the art would recognize.

A single pump effectively produces a 4-way pumping action which is useful to augment Fontan TCPC flow. Preliminary designs have been demonstrated and published to induce pressure differential of 2-10 mmHg in the nominal operating range (3-7K RPM, with capabilities of generating higher pressure (up to 40 mmHg) at higher rotational speeds in the unlikely event of pulmonary hypertension). Further, the pump has greatly reduced potential to obstruct flow in the Fontan venous pathway. Even when non-rotational, the impeller continues to serve a streamlining function to passive flow through the TCPC, reducing the hydraulic energy loss within the 4-way junction.

Figure 2:
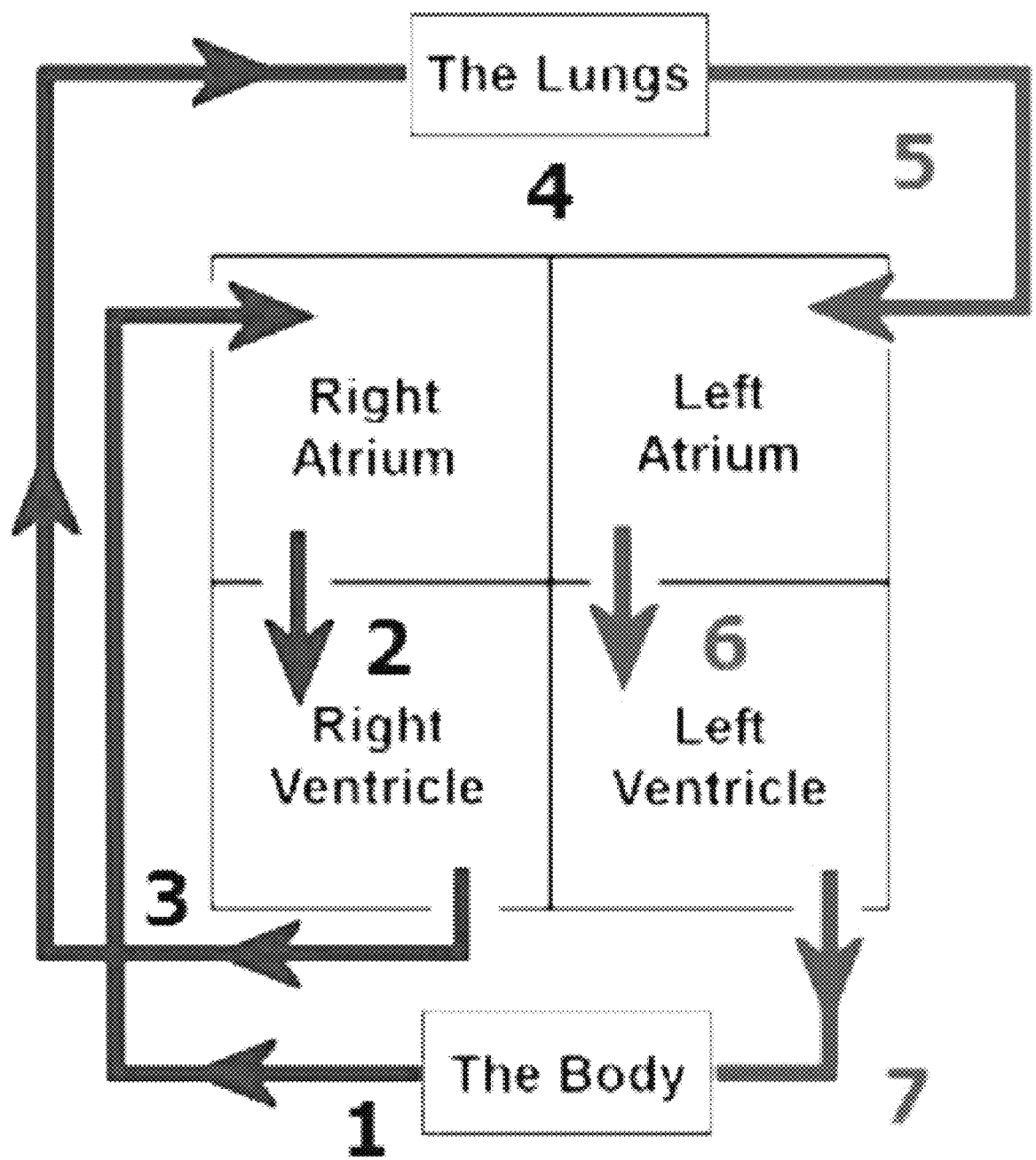
FIG. 2 is another schematic representation of the human circulatory system of FIG. 1, presented in block diagram format.

FIGS. 1 and 2 depict schematic representations of the circulatory system of a human being. Various embodiments of the present invention pertain to such circulation systems, as well as to circulatory systems of any biological unit.

Figure 3:
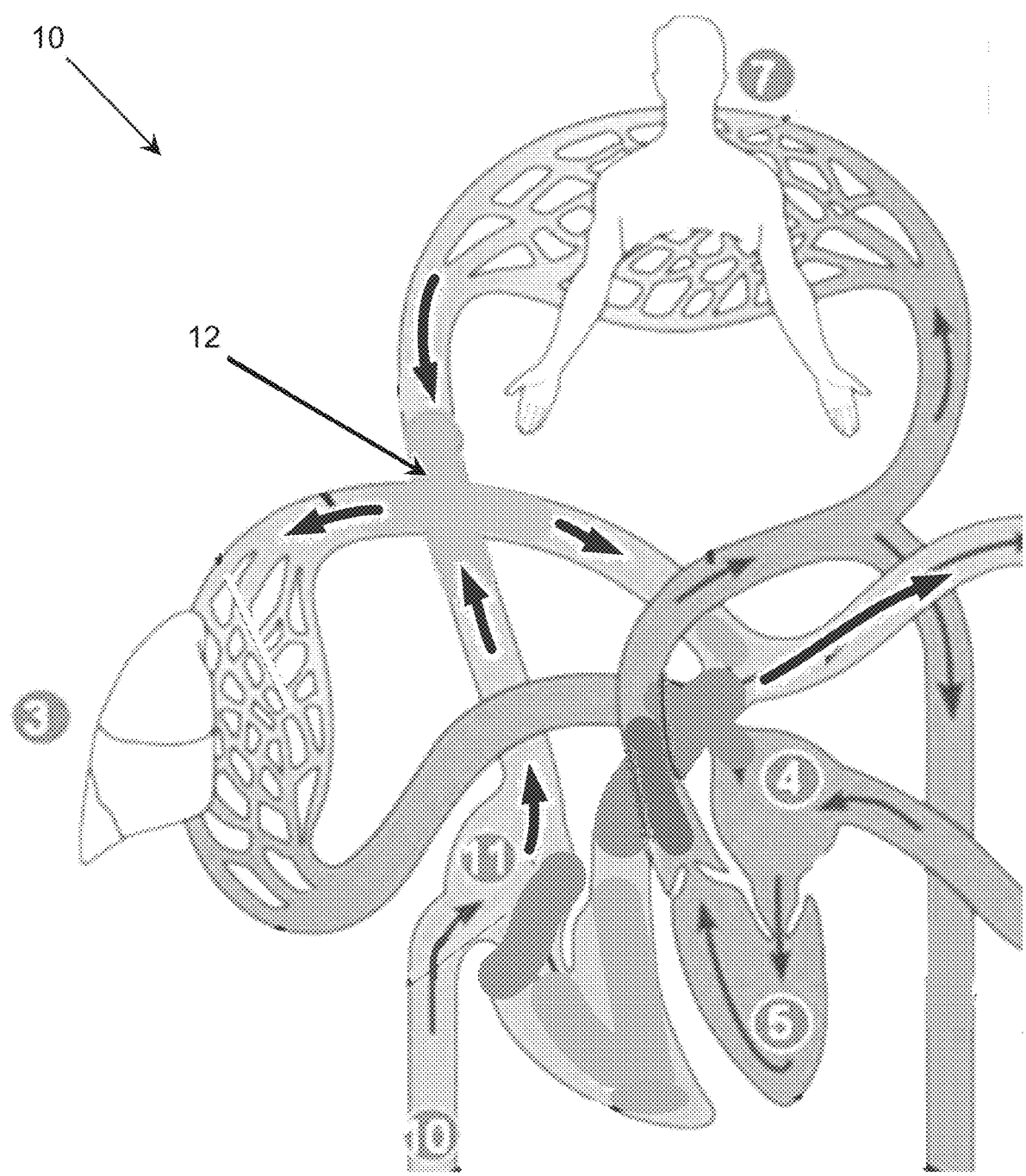
FIG. 3 shows the circulatory system of FIG. 1 as modified in accordance with Fontan procedures.

FIG. 3 schematically depicts a reconstructed human circulatory system as modified by the Norwood, Hemi-Fontan, and Fontan procedures.

Figure 4:
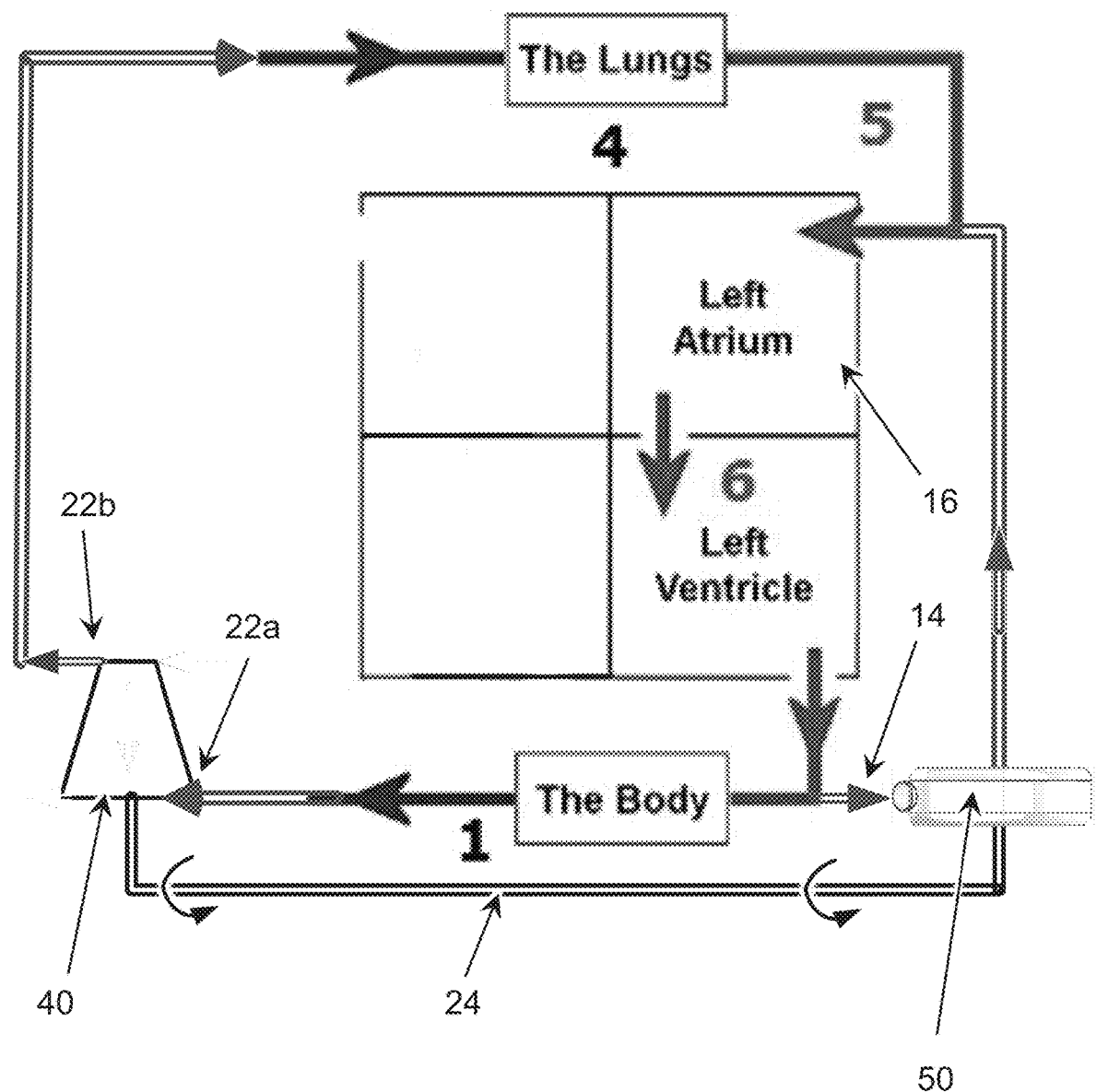
FIG. 4 is a block diagram that schematically represents the circulatory system of FIG. 3 and that also includes an implanted pumping assembly according to one embodiment of the present invention.

FIG. 4 schematically shows the biologic flow system and the placement and interconnection of an implantable pumping assembly 20 according to one embodiment of the present invention. Pumping assembly 20 preferably includes a hydraulic motor 50 that includes means for providing power by action of a fluid boundary layer. In some embodiments, motor 50 is a type of multi-disk motor that is related to a Tesla motor.

Motor 50 is interconnected by a shaft 24 to impart power to at least one rotatable pump 40. It can be seen in FIG. 4 that in the context of a Fontan application, the inlet to the motor 50 receives blood at a higher pressure 14 (as shown coming from the left ventricle). After imparting power to drive pump 40, the blood exits motor 50 from a central region 54b, which is in fluid communication to a source of lower pressure 16, such as the oxygenated blood provided from the lungs to the left atrium.

FIG. 4 further shows that blood at a pressure lower than higher pressure source 14 (i.e., by way of a pressure drop after passage through the body) is provided to the inlet 22a of pump assembly 20. The rotation of pump 40 results in an energy increase in the pumped blood that exits from outlet 22b, which is shown being provided to the lungs.

FIG. 5 presents a partially cutaway schematic representation of a pumping assembly 20 according to one embodiment of the present invention. It can be seen that assembly 20 includes a centrally located fluid motor 50 that is rotatable along the axis of a shaft 24 having two ends (top and bottom, as shown in FIG. 5). Each end of shaft 24 is rotatably supported by a bearing 26 that in turn is statically supported by a housing 22.

Located on opposing sides of motor 50 are first and second (top and bottom in FIG. 5) pumping elements 40. Each of these pumping elements are interconnected to motor 50 so as to be provided with motive power by motor 50, such that the pumping assembly 20 rotates in unison.

FIG. 5 further shows the fluid pathways that provide blood to motor 50. The higher pressure source 14 flows in a conduit 25 to the periphery of a rotatable stack 54 comprised of a plurality of plates or disks 56. In some embodiments, the fluid from source 14 is provided to a manifold 25d that extends around the circular periphery 54a of stack 54. Preferably, the fluid conduit 25, including the manifold 25d, are retained by housing 22 in a static position relative to housing 22. Preferably, the interface between the static manifold and the rotating stack 54 is adapted and configured to minimize both leakage and friction.

Preferably, flow conduit 25 includes a nozzle 25c that directs the fluid in a direction that is at least partly tangent to periphery 54a. Fluid flowing through this nozzle (and also fluid anywhere within manifold 25b) is able to flow radially inward from periphery 54a of stack 54 toward the center 54b (as indicated by turning arrows). This radially inward flow is encouraged by connection of the higher pressure source 14 to a lower pressure source 16, the lower pressure source 16 being in fluid communication with the central portion 54b of the stack 54.

Figure 8:
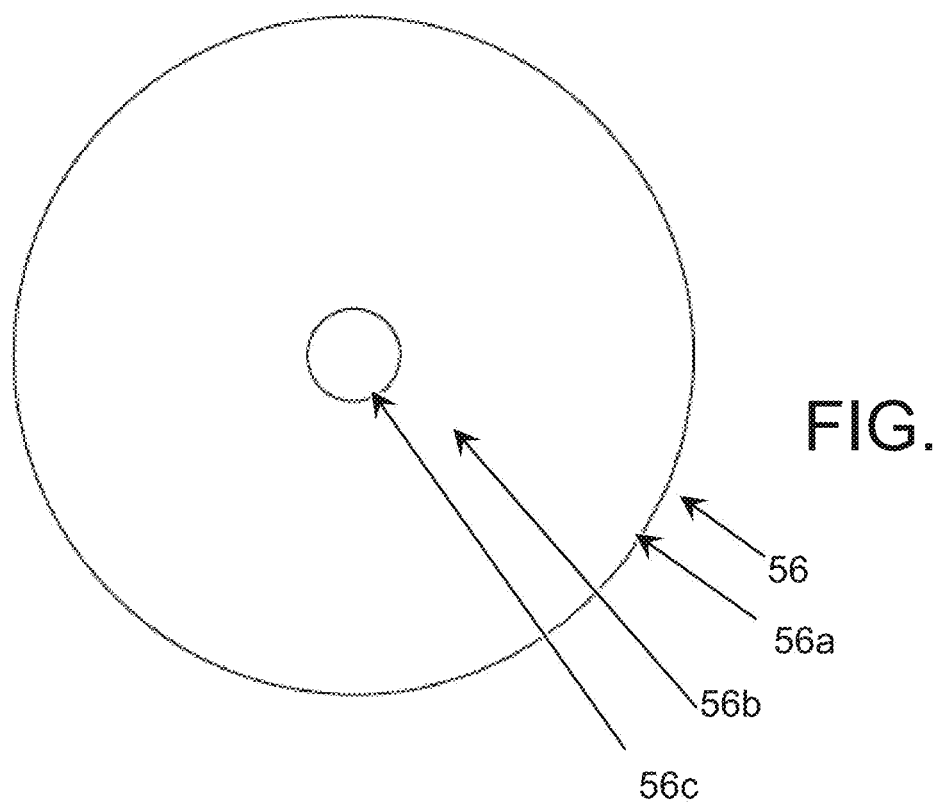
FIG. 8 is a top plan view of a disk used in the motor of the apparatus of FIG. 5.

Referring to FIG. 8, it can be seen that preferably a plurality of generally flat, smooth disks 56 are centered about the rotational axis of the shaft, and further placed on opposing sides of each other in a generally parallel arrangement (as indicated in FIG. 5). FIG. 8 further shows that in some embodiments preferably each of the plates 56 include a flow exit 56c or aperture through which the radially inflowing fluid is collected.

Referring back to FIG. 5, it can be seen that the collection of the flow exits 56c of the plates direct the collected radially inflowing fluid to the draining flowpath 54c of stack 54. As indicated by the centrally located turning arrows of FIG. 5, this flow from the center apertures of the plates is directed to the hollow portion 24b of shaft 24. Fluid is unable to go in the opposite direction along shaft 24 (up as shown in FIG. 5) because that portion 24a of the shaft is preferably solid, and not permitting internal flow, although in yet other embodiments the shaft includes hollow portions that extend in both directions along the shaft.

FIG. 5 shows that flow leaves the hollow portion 24b of shaft 24 through a drain connection 24c, which includes an outlet conduit that is in fluid communication with the lower pressure source 16. In this manner thus described, a fluid pressure differential of a flowing fluid from one inlet conduit receiving source 14 to an outlet conduit in communication with source 16 provides fluid power to motor 50. Still further embodiments include a second outlet conduit and second hollow portion to direct fluid from the stack in two opposing directions.

As a result of the power imparted to motor 50, the pumping elements 40 on opposite sides of the motor 50 are driven to rotate. As shown in FIG. 5, pumping elements 40 are represented to have a viscous impelling surface 42. Flow from the central, outermost diameter of pumps 40 (i.e., proximate to manifold 25b) eject flow in an outward manner (laterally in FIG. 5) through opposing outlets 22b. This ejection results in a draw of fluid from opposing inlets 22a to the entrance of the pumping elements 40 (i.e., near the bearings 26 and near the drain 24c). The flow arrows 29 indicate the overall direction of flow external to pumping elements 40.

Although what has been shown and described in FIG. 5 is a pumping assembly 20 that includes a pair of VIP pumping elements 40, it is further understood that assembly 20 can further include any kind of centrifugal pumping element X40 (including those shown herein), and further including pumping assemblies that include a single pumping element driven by a motor X50.

Figure 6:
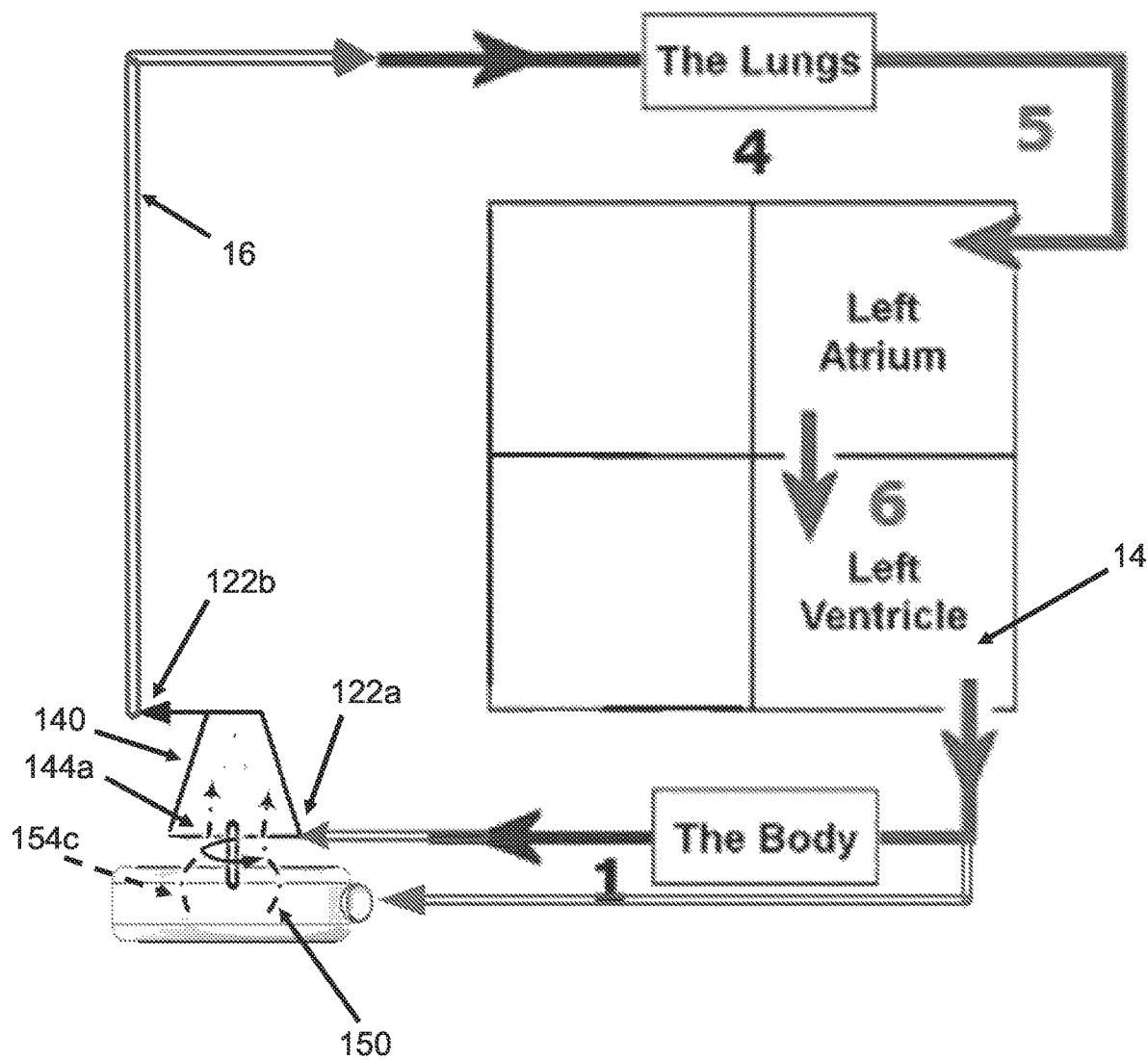
FIG. 6 is a block diagram that schematically represents the circulatory system of FIG. 3 and that also includes an implanted pumping assembly according to another embodiment of the present invention.

FIG. 6 shows a circulation system with the same Fontan modification as shown previously but incorporating an implantable pumping assembly 120 according to another embodiment of the present invention. Pumping 120 includes a hydraulic motor 150 that in some embodiments uses a flow of pressurized blood to create a motive force that drives one or more pumping assemblies 140. In a manner similar to that shown in FIG. 4, motor 150 receives fluid from a source 14 at a higher pressure, and pump 140 receives blood at a lower pressure through inlet 122a. Motor 150 drives pump 140 to rotate and provide fluid at an outlet 122b that is in fluid communication with a source 16. At least one difference between pumping assemblies 20 and 120 is that the fluid exiting from the drain flowpath 154c of stack 154 is provided to a surface 144a of pump 140.

Further details of pumping element 120 can be seen in FIG. 7, which shows a pumping assembly 120 having a rotating assembly comprising a pair of pumping elements 140 arranged on opposite sides of a motor 150, this assembly being retained by bearings in a manner similar to that of pump 120. In a manner similar to that shown for pump assembly 20, it can be seen that fluid at the higher pressure 14 is provided to a peripheral manifold 125d. At least one other difference relative to assembly 20 is that shaft 124 preferably does not have a hollow section providing an internal flowpath.

Each of the pumping elements 140 preferably include one or more discrete ridges or blades 144 that extend outwardly from a surface base 144a. Although what is shown and described for FIG. 7 are a plurality of blades 144 extending vertically along the rotational axis of shaft 124, it is understood that these blades can further be ridges that are less prominent than the blades as shown, and further that these ridges can be incorporated into a surface 144a that is adapted and configured to provide some measure of centrifugal pumping. It is further understood that the pump X40 can be utilized with either of the motors X50.

In one embodiment, the surface 144a of each pump 140 includes an outlet aperture 146a that receives fluid from an internal flow passage 146. This flow passage 146 in turn receives fluid from a draining flowpath 154c located within a central region of stack 154.

Figure 9:
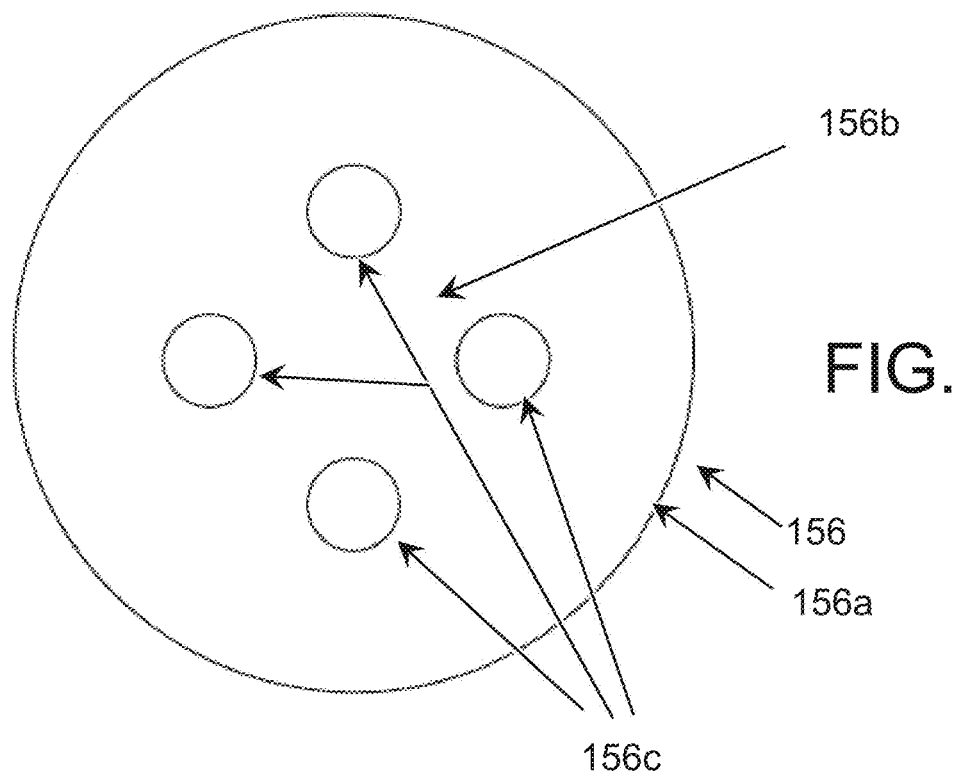
FIG. 9 is a top plan view of a disk used in the motor of the apparatus of FIG. 7.

Referring briefly to FIG. 9, a plate 156 includes at least one through hole or flow exit 156c providing fluid to stack drain 154c and that permits the passage of the radial input of fluid within motor 150 toward these flow exits and toward the central portion 156b of the plate.

Returning to FIG. 7, it can be seen that the flow exits 156c provide fluid communication to an internal flow passage 146 within pump 40. Preferably, the exits 146a are located in a region of relatively low static pressure on surface 144a, such that fluid provided to the periphery of stack 154 by way of manifold 125d flows radially inward (as indicated by the turning arrows), and out through the outlets 146a of passages 146 and into the flow field of the pumping element 140.

FIGS. 10A, 10B, and 10C present schematic representations of different configurations of motors X50 driving impellers X40. It is understood that other features of the pumping assemblies 220, 320, and 420 are generally discussed herein with regards to other pumping assemblies X20.

FIG. 10A represents a centrifugal pump 240 being driven by a shaft 224 receiving motive power from a motor 250. Flowpaths 29 indicate the direction of flow of the pumped from inlet to outlet. In some embodiments, impeller 240 is similar to the impellers 40 and 140 described herein, except that the motor 250 is located externally to the impeller 240. A shaft 224 extends out of motor 250 and is coupled to impeller 240 to cause the impeller to rotate. In some embodiments, the impeller 240 is located within a housing 222 (not shown) similar to housings 22 and 122. Similar to the configurations 20 and 120 shown and discussed previously, fluid used by motor 250 for generation of motive power can be circulated as shown and described with FIGS. 4 and 6.

FIG. 10B represents a centrifugal pump 340 being driven by a shaft 324 receiving motive power from a motor 350. Flowpaths 29 indicate the direction of flow of the pumped from inlet to outlet. In some embodiments, impeller 340 is similar to the one side of the impellers 40 and 140 described herein. In some embodiments motor 350 is located externally to the impeller 340, and the motor drives the impeller from the outflow side of the impeller. A shaft 324 extends out of motor 350 and is coupled to impeller 340 to cause the impeller to rotate. In some embodiments, the impeller 340 is located within a housing 322 (not shown) similar to half of housings 22 and 122 with regards to the internal housing flowpath. In still further embodiments motor 350 is located within the housing 322, although it is further contemplated that the motor 350 can be located externally to the housing. Similar to the configurations 20 and 120 shown and discussed previously, fluid used by motor 350 for generation of motive power can be circulated as shown and described with FIGS. 4 and 6.

FIG. 10CB represents a centrifugal pump 440 being driven by a shaft 424 receiving motive power from a motor 450. Flowpaths 29 indicate the direction of flow of the pumped from inlet to outlet. In some embodiments, impeller 440 is similar to the one side of the impellers 40 and 140 described herein. In some embodiments motor 450 is located externally to the impeller 440, and the motor drives the impeller from the inflow side of the impeller. A shaft 424 extends out of motor 450 and is coupled to impeller 440 to cause the impeller to rotate. In some embodiments, the impeller 440 is located within a housing 422 (not shown) similar to half of housings 22 and 122 with regards to the internal housing flowpath. In still further embodiments motor 450 is located within the housing 422, although it is further contemplated that the motor 450 can be located externally to the housing. Similar to the configurations 20 and 120 shown and discussed previously, fluid used by motor 450 for generation of motive power can be circulated as shown and described with FIGS. 4 and 6.

While the inventions have been illustrated and described in detail in the drawings and foregoing description, the same is to be considered as illustrative and not restrictive in character, it being understood that only certain embodiments have been shown and described and that all changes and modifications that come within the spirit of the invention are desired to be protected.

What is claimed is:

1. A method for pumping fluid within a human, comprising:
    operating a pumping assembly comprising a fluid motor and a fluid pump, the fluid motor including a first member being rotatable about an axis and having a first surface perpendicular to the axis, a second member being rotatable about the axis and having a second surface perpendicular to the axis, the second surface facing the first surface and being spaced apart from the first surface by a gap, the fluid pump including a first rotatable pumping element and a second rotatable pumping element, the first member and the second member being located between the first pumping element and the second pumping element, the fluid motor and the fluid pump being interconnected to rotate in unison about the axis;
    providing fluid at a first pressure to the periphery of the fluid motor;
    flowing the fluid from the periphery of the fluid motor toward the axis;
    draining the fluid at a second pressure lower than the first pressure from a central region of the fluid motor located radially inward of the periphery; and
    inducing rotation of the pumping assembly during said flowing by fluid drag on the first surface and the second surface.

2. The method of claim 1 which further comprises a shaft located along the axis and including a hollow portion, said shaft interconnecting the first member, second member, first pumping element and second pumping element, said draining being through the hollow portion.

3. The method of claim 1 wherein said first pumping element includes a first flow passage providing fluid communication from the central region to the first pumping surface, and which further comprises flowing the drained fluid from the central region to at least one of the first pumping element or the second pumping element.

4. The method of claim 1 in which the first surface and the second surface are substantially planar.

5. An implantable apparatus for pumping fluid in a human, comprising:
    a fluid motor adapted and configured for converting a pressure differential of a flowing fluid into rotational energy, said fluid motor including a plurality of plates in parallel alignment in a stack rotatable about an axis, said fluid motor having two opposing sides, said fluid motor having a motor fluid inlet located along the periphery of the stack and a fluid motor outlet located centrally within the stack;
    a first pumping element located on one side of said fluid motor and being driven to rotate by said fluid motor; and
    a second pumping element located on the other side of said fluid motor and being driven to rotate by said fluid motor;
    wherein fluid at a higher pressure is provided to the fluid motor inlet, flows within the stack, and is drained from the fluid motor outlet to the fluid at a lower pressure.

6. The apparatus of claim 5 wherein fluid from the fluid motor outlet is provided to at least one of said first pumping element and said second pumping element.

7. The apparatus of claim 5 which further comprises a shaft rotatably supporting said fluid motor, said first pumping element and said second pumping element for rotation about the axis.

8. The apparatus of claim 7 wherein said shaft includes a hollow portion that provides fluid communication from within the stack to the motor outlet.

9. The apparatus of claim 5 which further comprises a manifold supported by said housing that sealingly surrounds the stack and provides fluid at the higher pressure to the motor fluid inlet.

10. The apparatus of claim 5 which further comprises a housing comprising a biocompatible material, said housing including at least one housing inlet providing the fluid to the first pumping inlet and the second pumping inlet, the first pumping element and the second pumping element each being located within the housing.

11. The apparatus of claim 5 wherein said first pumping element is a bladed centrifugal pump and said second pumping element is a bladed centrifugal pump.

12. The apparatus of claim 5 wherein said first pumping element is a viscous impeller pump and said second pumping element is a viscous impeller pump.

13. An implantable apparatus for pumping fluid in a human, comprising:
    a housing comprising a biocompatible material and adapted and configured for implantation in a human;
    a fluid motor located in said housing and adapted and configured for converting a pressure differential of a flowing fluid into rotational energy, said fluid motor including a plurality of plates in parallel alignment and rotatable about an axis, said plurality of plates having a centrally located fluid outlet;
    a manifold statically supported by said housing and surrounding the periphery of said plurality of plates, said manifold having an inlet and providing fluid from the manifold inlet to the plurality of plates;

a pump located in said housing and including a first centrifugal pumping element and a second centrifugal pumping element, said pump having a plane of symmetry with said first pumping element and said second pumping element being located on opposite sides of the plane of symmetry, said pump being driven to rotate by said fluid motor;

wherein fluid at a higher pressure is provided to the manifold inlet, flows between said plurality of plates, and is drained from the centrally located fluid outlet.

14. The apparatus of claim 13 which further comprises a shaft rotatably supporting said fluid motor and said pump for rotation about the axis.

15. The apparatus of claim 14 wherein said shaft includes a hollow portion that provides fluid communication from within the stack to the fluid outlet.

16. The apparatus of claim 13 wherein said housing includes a first housing inlet providing the fluid to the first centrifugal pumping inlet and a second housing inlet providing the fluid to the second pumping inlet, said first housing inlet and said second housing inlet being located on opposite sides of said housing.

17. The apparatus of claim 13 wherein said first pumping element is a viscous impeller pump and said second pumping element is a viscous impeller pump.

18. The apparatus of claim 13 wherein said first pumping element and said second pumping are each axisymmetric about the rotational axis.

* * * * *